United States Patent
Nüsser et al.

(10) Patent No.: US 6,719,791 B1
(45) Date of Patent: Apr. 13, 2004

(54) DEVICE FOR THE AXIAL TRANSPORT OF FLUID MEDIA

(75) Inventors: Peter Nüsser, Berlin (DE); Johannes Müller, Berlin (DE); Hans-Erhard Peters, Berlin (DE); Norbert Buske, Berlin (DE); Werner Neumann, Berlin (DE); Kurt Graichen, Berlin (DE); Conrad Kauffeldt, Berlin (DE)

(73) Assignee: Berlin Heart AG, Berlin (DE)

( * ) Notice: Subject to any disclaimer, the term of this patent is extended or adjusted under 35 U.S.C. 154(b) by 0 days.

(21) Appl. No.: 09/959,044

(22) PCT Filed: Apr. 19, 2000

(86) PCT No.: PCT/EP00/03562
§ 371 (c)(1),
(2), (4) Date: Dec. 31, 2001

(87) PCT Pub. No.: WO00/62842
PCT Pub. Date: Oct. 26, 2000

(30) Foreign Application Priority Data
Apr. 20, 1999 (DE) .......................... 199 18 840

(51) Int. Cl.⁷ .......................... A61M 1/10; F04B 17/00; A61N 1/362
(52) U.S. Cl. .................. 623/3.13; 600/16; 417/423.11; 415/900
(58) Field of Search .............. 604/7–9, 93.01, 604/151, 154; 623/3.13, 3.14, 3.26; 415/900; 417/355, 356, 423.11, 423.12, 423.13; 600/16–18

(56) References Cited

U.S. PATENT DOCUMENTS

| | | | | |
|---|---|---|---|---|
| 4,625,712 A | * | 12/1986 | Wampler | 600/16 |
| 4,704,121 A | * | 11/1987 | Moise | 623/3.13 |
| 4,846,152 A | * | 7/1989 | Wampler et al. | 600/16 |
| 4,908,012 A | * | 3/1990 | Moise et al. | 600/16 |
| 5,112,200 A | * | 5/1992 | Isaacson et al. | 417/356 |
| 5,211,546 A | * | 5/1993 | Isaacson et al. | 417/536 |
| 5,692,882 A | * | 12/1997 | Bozeman et al. | 417/45 |
| 5,911,685 A | * | 6/1999 | Siess et al. | 600/16 |
| 5,957,672 A | * | 9/1999 | Aber | 417/423.12 |
| 6,018,208 A | * | 1/2000 | Maher et al. | 310/254 |
| 6,116,862 A | * | 9/2000 | Rau et al. | 417/319 |
| 6,135,729 A | * | 10/2000 | Aber | 417/420 |

FOREIGN PATENT DOCUMENTS

| | | | | |
|---|---|---|---|---|
| DE | 19613565 | * | 7/1997 | A61M/1/12 |
| DE | 19613564 | * | 1/1998 | A61M/1/12 |

* cited by examiner

Primary Examiner—LoAn H. Thanh
Assistant Examiner—Catherine S. Williams
(74) Attorney, Agent, or Firm—Norris McLaughlin & Marcus

(57) ABSTRACT

The invention provides a device for the axial delivery of fluidal mediums, which outer diameter is not or only insignificantly larger than the diameter of the fluid carrying pipe, which reduces to a large extent a shearing and vortexing of the fluid. A device for the axial delivery of fluidal mediums, having a tubular hollow body arrangement, in which delivery area, an impeller (9) with a blading, which can be rotated, is arranged and also has a fluid directional means. A motor (2), at least one impeller (9) which can be rotated, and at least one motor mounting (14) are arranged in a tubular hollow body (1) of the hollow body arrangement. The impeller (9) is connected axially force-fittingly and/or form-fittingly to the motor (2).

18 Claims, 5 Drawing Sheets

DEVICE FOR THE AXIAL TRANSPORT OF FLUID MEDIA

BACKGROUND OF THE INVENTION

The invention relates to a transport of fluid media.

Devices according to the state of the art are preferably used as pumps for the gentle delivery of body fluids in the medical field, in chemical, biological and/or bio-chemical processes. Special importance have these pumps as blood pumps for the support of an ill heart, which can be implanted into the chest area of a patient.

In the publication "Heart Replacement Artificial Heart 5", pages 245–252, Springer Verlag Tokyo 1996, Publishers T. Akutso and H. Koyagani, a blood pump delivering axially for the support of an ill heart is described. This blood pump has a rotating impeller with a blading, which is mounted within a pipe carrying blood and is driven by means of an electric motor. For this the impeller is formed as a rotor of the electric motor and is coupled by means of magnets mounted on the blading with the stator of the electric motor and mounted outside the pipe. Such an arrangement is known from U.S. Pat. No. 4,957,504. In front of and behind the impeller, respectively, stator units with a stator grid (stator blades) are arranged, attached to the casing and serving for influencing the flow. The pump described there has different disadvantages. Because of the spatial separation in the motor, i.e. of the stator and the impeller of the electric motor, considerable losses in power of the electric motor are caused. A further disadvantage is caused by the arrangement of the stator of the electric motor outside of the blood carrying pipe. The unavoidable volume increase of the whole device caused by this can impair the implantability. Furthermore, the delivered blood experiences in a considerable extent a traumatisation and damage. This is especially caused by the shearing and vortexing of the blood, caused by the gaps between the outer edge of the blading and the inner side of the pipe carrying blood, as well as by the arrangement of the axial bearings.

From Yoshinori Mitamura et al, The Valvo Pump, An Axial Non-Pulsatile Blood Pump, Asaio Transactions, Vol. 37 (1991), No. 3, p. 510–512 a blood pump is known, consisting of a tubular hollow body arrangement, in which delivery area an impeller with a blading, which can be rotated, and a motor with motor mounting are arranged. The motor mounting is formed as a fluid stator unit. The impeller is axially force-fittingly and form-fittingly connected to the impeller. The shaft is sealed at its bearing with a teflon-seal or with a magnetic particle seal. Even here gaps occur, in which the blood is traumatised.

SUMMARY OF THE INVENTION

The invention is based on the object to provide a device for the axial delivery of fluidal mediums, which reduces as far as possible a shearing and vortexing of the fluid.

The object is solved according to the invention by a device for the axial delivery of fluidal mediums comprising
a tubular hollow body arrangement, in which delivery area, an impeller (9) which can be rotated is arranged having blading and fluid directional means, characterised in that
a motor (2), at least one impeller (9) which can be rotated, and at least one motor mounting (14) are arranged in a tubular hollow body (1) of the hollow body arrangement, wherein the impeller (9) is connected axially force-fittingly and/or form-fittingly with the motor (2).

Another embodiment shows the device the motor mounting formed as a stator (14), characterised in that the stator (14) is mounted on an inner pipe wall (8) of the tubular hollow body (1).

Another embodiment displays the motor (2) formed as an electric motor characterised in that the electric motor (2) is integrated in a stator (14).

Another embodiment displays the mounting of the stator (14) having a flow feed (11) and are formed as stator blades (3).

Another embodiment shows a hub gap (13) formed by the motor side end face of the impeller (9) and by the impeller side end face of the stator (14) which comprises at least one annular seal (5).

Another embodiment of the invention shows the device having a seal (5) which consists of a magnet arrangement (30) and of a magnetic liquid (31) hold by it, where the seal (5) is formed as a magnetic particle seal. In a further embodiment, the magnetic particle seal is combined with at least one seal of the state of the art.

Another embodiment shows the device characterized by a magnet arrangement (30) which consists of a magnet (32) and two pole shoes (33, 34) forming an annular gap (36) and having a different magnetic charge, between which end faces (37, 38) a magnetic liquid (31) is arranged, wherein the magnet (32), the pole shoe (33) and/or the pole shoe (34) are fixed on the impeller (9) and/or on the electric motor (2). The Dole shoe (33 or 34) is formed in two pieces, separated by a secondary gap (35). The magnets (32) of the magnet arrangement (30) are formed as permanent or electromagnets.

Another embodiment shows end faces (37, 38) limiting the annular gap (36), between which the magnetic liquid (31) is arranged, formed mirror symmetrically to each other. It is further contemplated the end faces (37, 38) delimiting the annular gap (36) are not formed symmetrically to each other.

Another embodiment shows the end faces (37, 38) having recesses and/or projections which are formed circumferentially. A further embodiment displays a device where the end faces (37, 38) circumferentially are formed concave and/or convex.

Another embodiment shows the end faces (37, 38) are arranged parallel to each other. The end faces (37, 38) can also be arranged not parallel to each other. It is also contemplated that the end faces (37, 38) are formed planar.

Another embodiment of the invention shows the end faces (37, 38) arranged at a right angle to the annular gap axis. A further embodiment displays the end faces (37, 38) arranged acute-angled and/or obtuse-angled to the annular gap axis.

The invention relates to a tubular fluid carrying hollow body comprising a motor, which for example can be formed as an electric motor, an impeller with blading and a mounting for the motor, which can be formed as a stator. The impeller is force-fittingly and/or form-fittingly axially connected to the motor.

The hub gap occurring between the impeller and the electric motor is sealed according to the invention by means of a seal, especially a magnetic particle seal to the motor. By means of the arrangement of a magnetic particle seal in the hub gap the otherwise common flow through the gap is prevented, so that the normally resulting shearing and vortexing is reduced as far as possible. Combinations with further known seals are possible.

Furthermore, the solution according to the invention prevents a mounting of the impeller in the flow areas. The mounting of the impeller is solely carried out on the motor shaft, so that, together with the magnetic particle seal, a contact of the bearing means with the flowing fluid is impossible.

A further advantage of the solution according to the invention is that no wake areas exists in the area of the impeller and of the stator. Possible wake areas in the hub gap between the impeller and the electric motor can be minimised by the arrangement of the magnetic particle seal in the outer areas of the hub gap.

The magnetic particle seal arranged according to the invention in the hub gap shows no abrasion and is free from wear and low-frictional. Magnetic liquids are stable dispersions with superparamagnetic characteristics. The dispersions consist generally of the magnetic component, of amphiphilic additives and a carrier liquid. For the magnetic component, ferrimagnetic or ferromagnetic particles are used, which particle size lies between 3 and 50 nm. Because of the so-called amphiphilic additives, the particles get, on the one hand, hydrophilic or hydrophobic characteristics and therefore can be homogenously dispersed either in aqueous or organic carrier liquids . For a carrier liquid, a liquid can be selected, which depending on the fluid to be delivered, shows no readiness of interaction. The composition of the magnetic liquid depends on the fluid to be delivered, in view of which the required saturation magnetisation, the viscosity and the chemical composition is determined. The saturation magnetisation determines the interaction of the magnetic liquid and the magnetic field. The stronger the magnetisation, the higher the pressure differences, which can be withstood by the magnetic particle seal with otherwise the same magnetic arrangement.

Advantageously, the magnetic particle seals can be provided with different carrier liquids. The spectrum of the usable liquids extends from water or liquids, mixable with water, to oil based and liquids non-soluble in water. Because of this, the character of the carrier liquid can be adapted to the character of the fluidal medium transported in the pipes. If, for example, aqueous liquids are delivered, it is appropriate, to use a magnetic liquid on the basis of oil, as the seal means and vice versa. The degree of the interactions between the fluid and the magnetic liquid assumes, in this case, with the support of the magnetic field towards zero, which is especially an exceptional advantage, when delivering and transporting biological and other sensitive fluids, like blood.

The possibility to use magnetic liquids on the basis of perfluorised polyethers even enables to deliver with the device according to the invention oil-in-water- or water-in-oil-emulsions, which have hydrophilic and hydrophobic characteristics and therefore can interact with an oil based or aqueous carrier liquid.

This seal has proven to be extremely low in friction, so that the energy expenditure for producing an axial rotation can be greatly minimised and a non-allowed warming of the medium to be delivered does not appear.

In an improvement of the invention an electric motor is integrated in a stator. The electric mains supply is carried out for example via the mountings of the stator on the inner wall of the tubular fluid carrying hollow body.

BRIEF DESCRIPTION OF THE DRAWINGS

Following the invention is described in detail by means of an embodiment with reference to the figures.

FIG. 2a to

DETAILED DESCRIPTION

Figure 1:
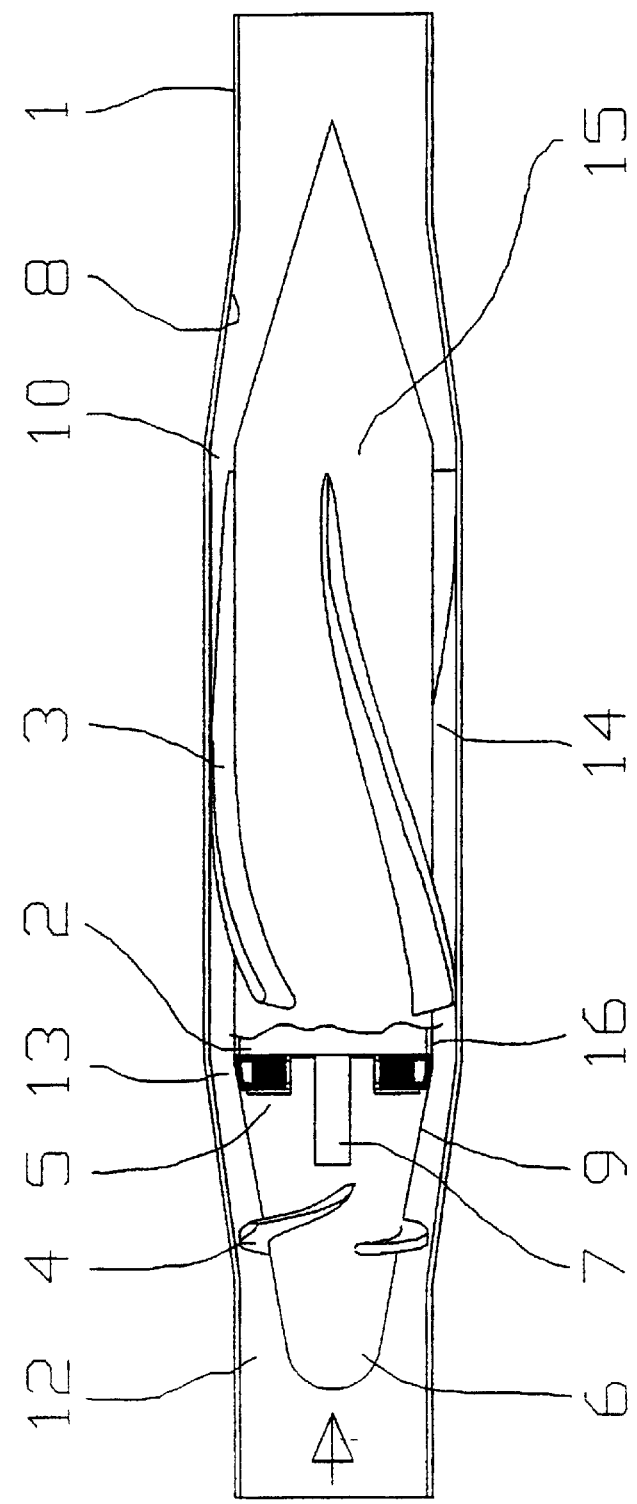
FIG. 1 shows a blood pump with an electric motor integrated in the stator.
Figure 2A:
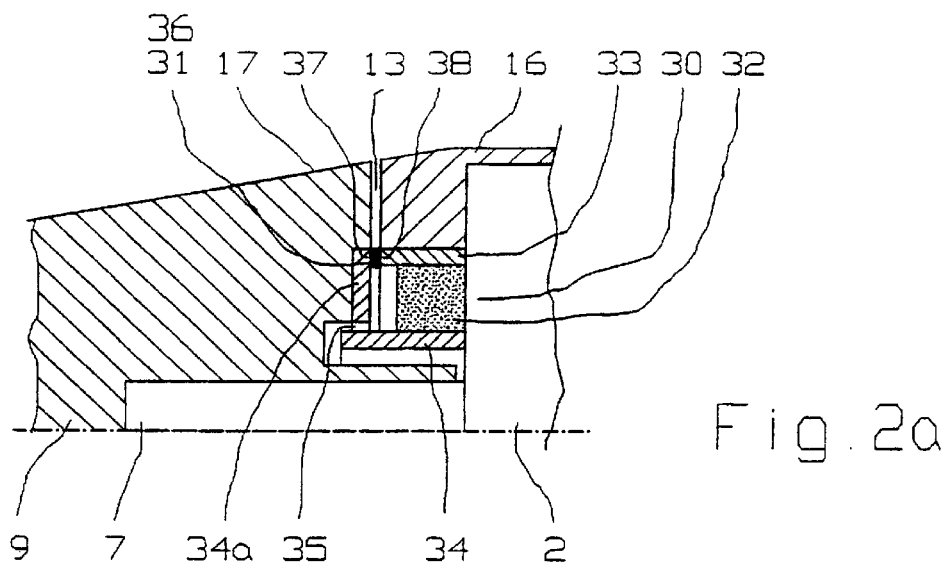
Figure 2B:
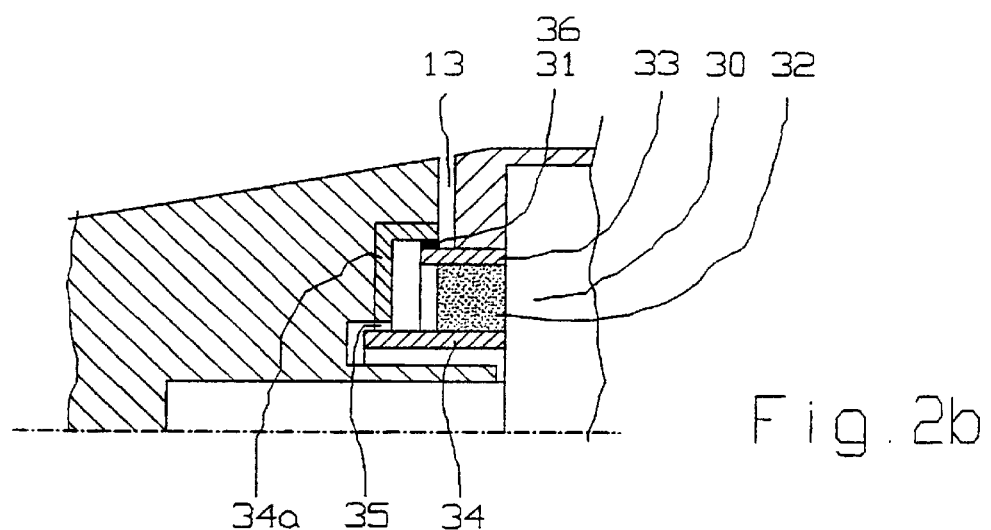
Figure 2C:
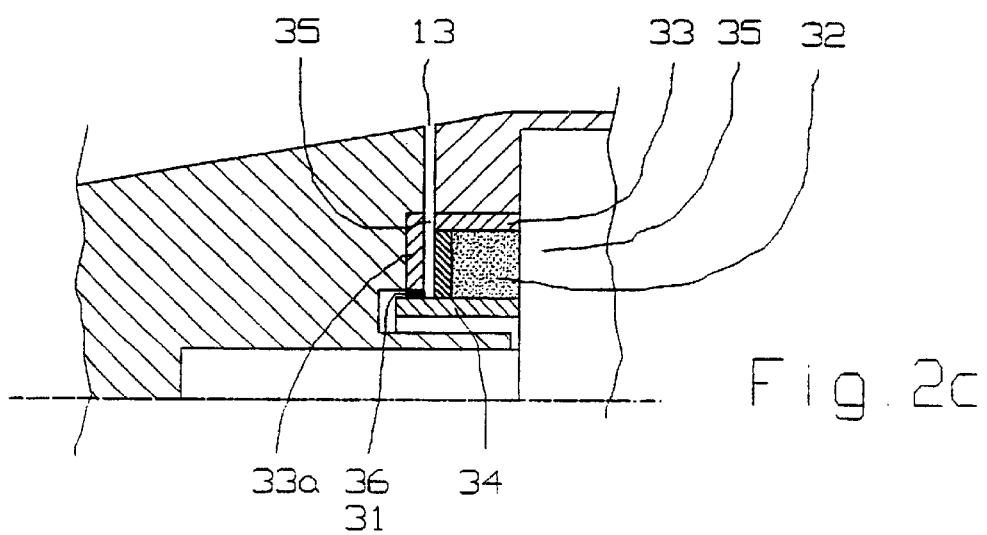
Figure 2D:
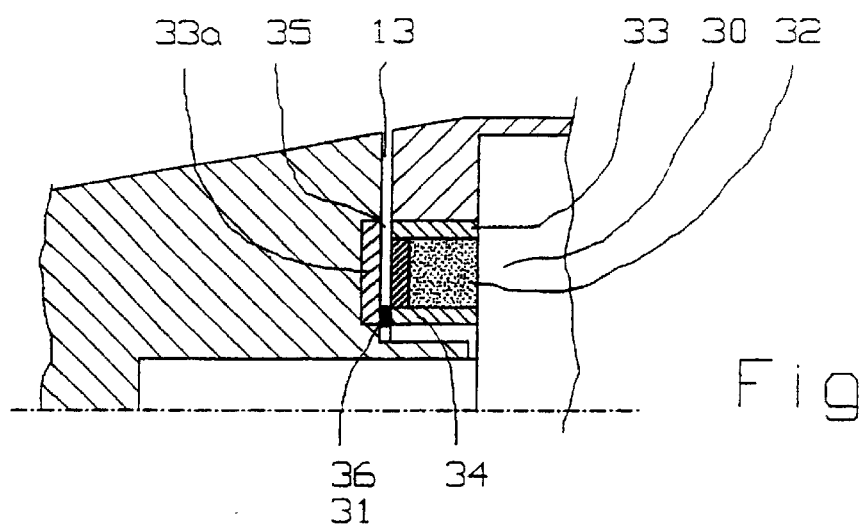
Figure 2E:
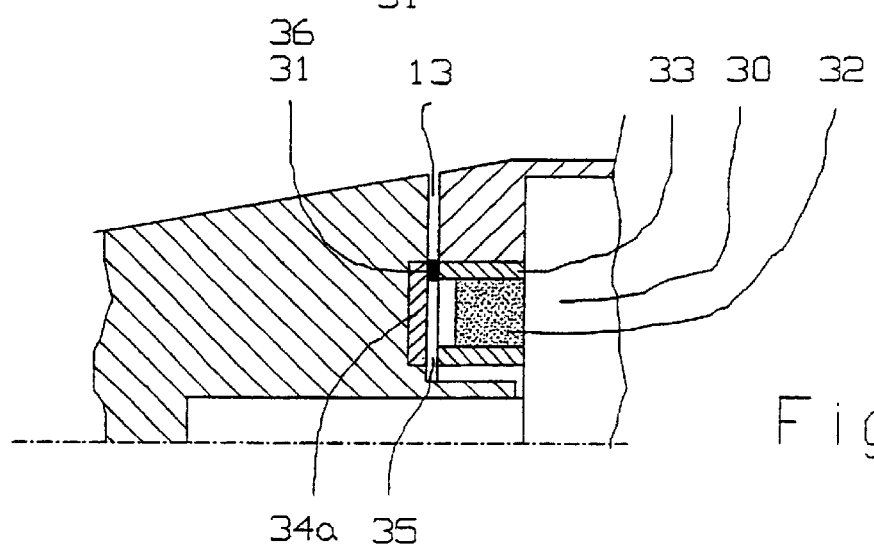
Figure 2F:
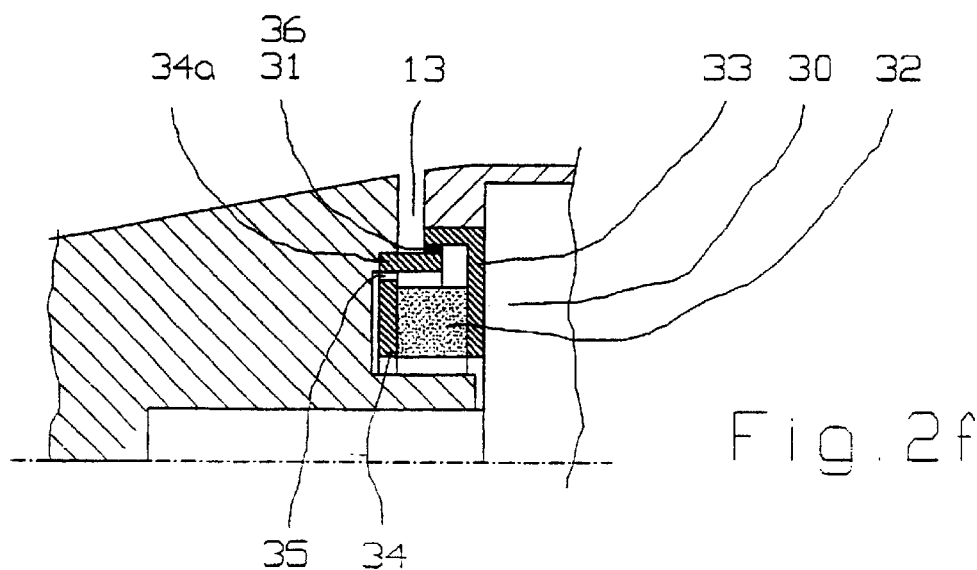
Figure 2G:
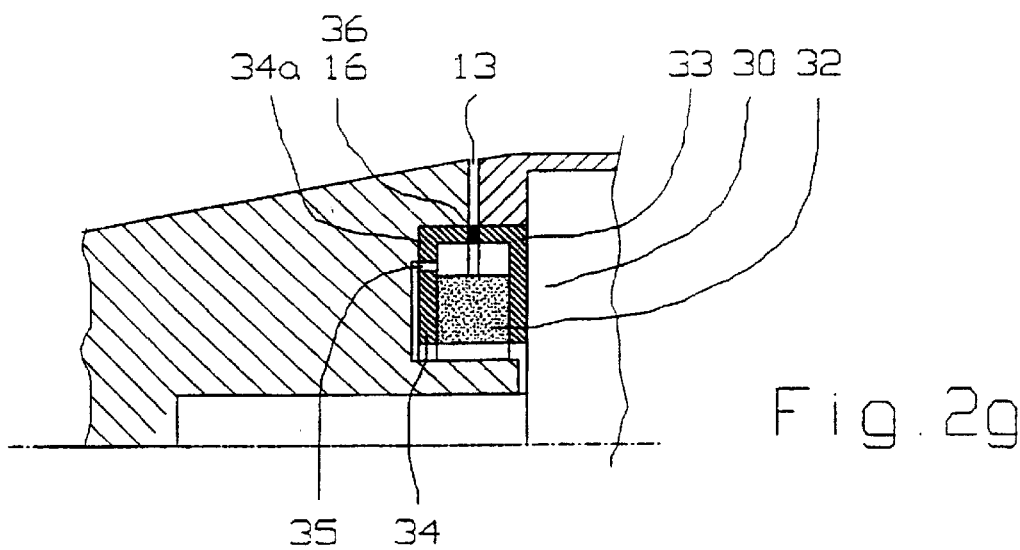
Figure 2H:
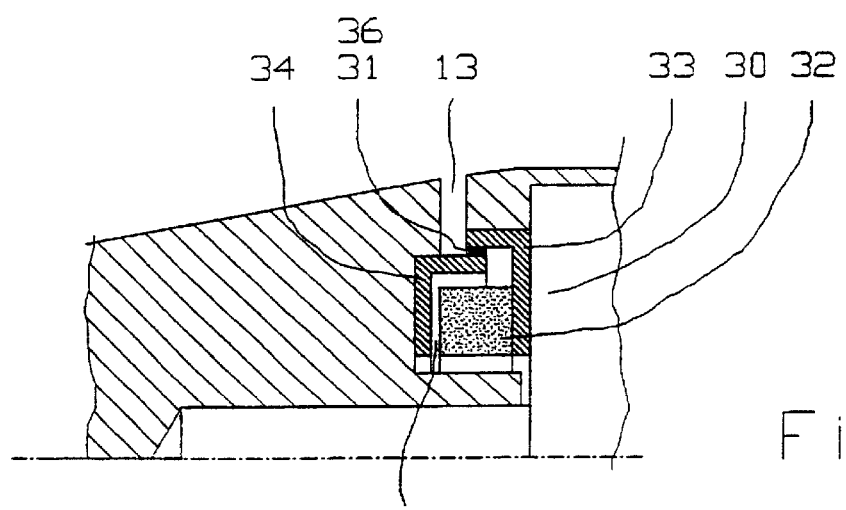
Figure 2I:
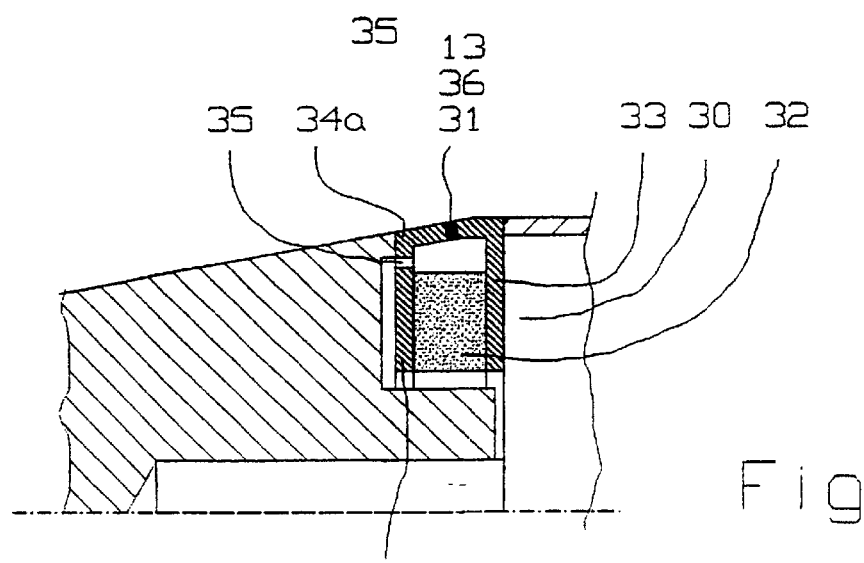
Figure 2J:
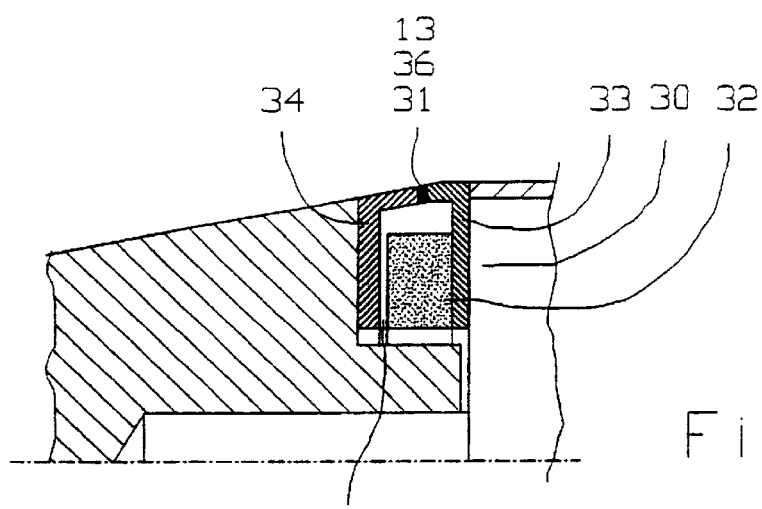
Figure 2K:
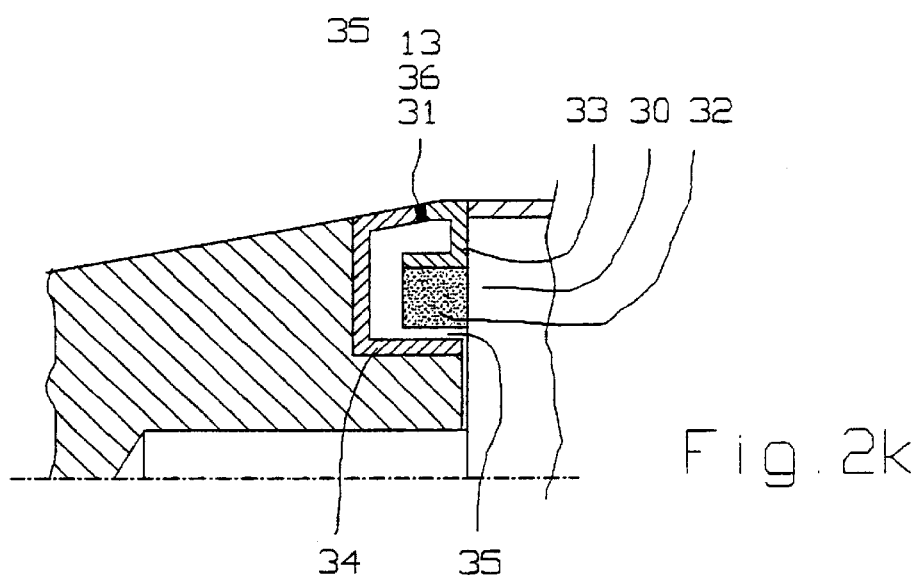
Figure 2L:
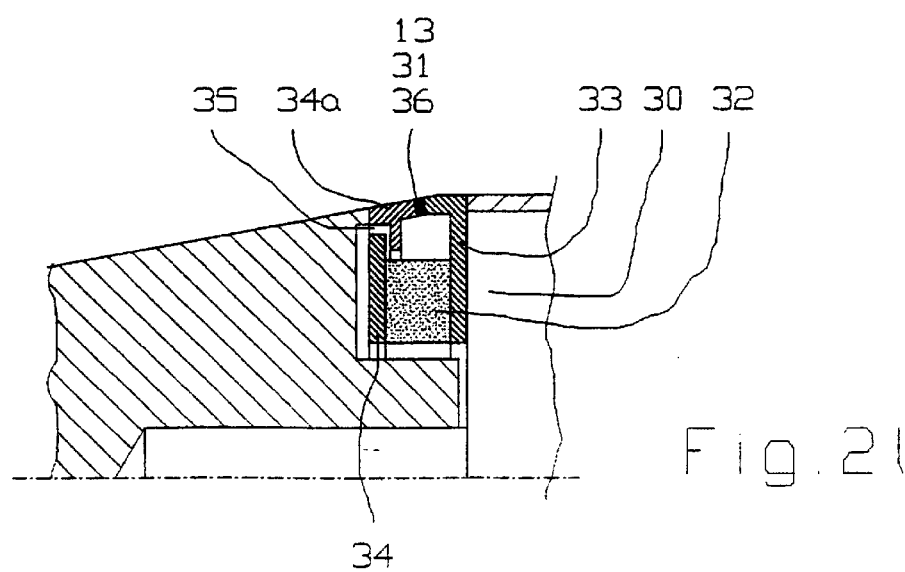
FIG. 2l show different schematical embodiments of the seal in the hub gap area.

FIG. 1 shows schematically an axial blood pump. An impeller 9 and a stator 14 are arranged in a tubular hollow body 1. An electric motor 2 is integrated in the stator 14. A motor shaft 7 of the electric motor 2 is connected to the impeller 9. Between the impeller 9 and the electric motor 2 a contact free zone, i.e. hub gap 13, is provided. The hub gap 13 is sealed by means of a seal 5 against the passing fluidal mediums. The actual seal medium is a magnetic liquid 31, which is held by means of a magnet arrangement 30 in the hub gap 13. The electric motor 2 drives the impeller 9 via the motor shaft 7. The electricity supply of the electric motor 2 is carried out via wires, not represented, through the mounting, which in this example serves as stator blades 3, on an inner pipe wall 8. In the area of the stator 14, the tubular hollow body 1 is formed with an expanded diameter. During the delivery, the impeller blades 4 deliver the blood passing the hub 6 into the rotational gap 12, which joins in the area of the stator 14 the flow area. The blood, which is rotated by means of the impeller blades 4, is redirected in the area of the stator blades to an axial direction and flows passed a stator hub 15 into the tubular hollow body 1.

FIGS. 2a to FIG. 2l show differently arranged seals 5. The seal 5 is arranged in both, in an impeller head 17 and a stator head 16. The impeller head 17 and the stator head 16 are separated from each other by the hub gap 13. Essentially the seal 5 consists of a magnet arrangement 30 with pole shoes 33 and 34, wherein one pole shoe always has separated areas 33a or 34a for forming a secondary gap 35, and a magnetic liquid 31, arranged in an annular gap, formed by the pole shoes 33 or 33a and 34 or 34a, respectively. The secondary gap 35 is formed in such a size, that a transmission of the magnetic field from the pole shoe 33 or 34 to a pole shoe 33a or 34a is possible, respectively, and that the free rotation of the impeller 9 is not hindered.

The sealing of the annular gap 36 by the magnetic liquid 31 is carried out radially or axially in the different representations. The secondary gap 35 is formed accordingly as well.

Reference Numerals List

1 Hollow body
2 Electric motor
3 Stator blade
4 Impeller blade
5 Seal
6 Impeller hub
7 Motor shaft
8 Inner pipe wall
9 Impeller
10 Flow area
11 Flow feed
12 Rotational gap
13 Hub gap
14 Stator
15 Stator hub
16 Stator head
17 Impeller head
30 Magnet arrangement
31 Magnetic liquid
32 Magnet
33 Pole shoe
33a
34 Pole shoe
34a
35 Secondary gap 36 Annular gap
37 End face
38 End face

What is claimed is:

1. Device for the axial delivery of fluidal mediums consisting of a tubular hollow body (1), in which a motor (2), at least one impeller (9) with blading which can be rotated and at least one motor mounting as well as fluid stator means are arranged, wherein the motor mounting is formed as a stator (14), wherein the stator (14) is mounted on an inner pipe wall (8) of the tubular hollow body(1), wherein the impeller (9) is connected axially force-fittingly and/or form-fittingly to the motor (2), wherein a hub gap (13) resulting between a motor-side front face of the impeller (9) and a impeller-side front face of the motor (2) is provided with at least one annular seal (5), wherein the seal (5) consists of a magnet arrangement (30) and a magnetic liquid (31).

2. Device according to claim 1, wherein the motor (2) is formed as an electric motor.

3. Device according to claim 1, wherein the motor (2) Is integrated in a stator (14).

4. Device according to claim 1, wherein the mountings of the stator (14) are formed as stator blades (3).

5. Device according to claim 1, wherein the seal (5) is formed as a magnetic particle seal.

6. Device according to claim 5, wherein the magnetic particle seal is combined with at least one seal.

7. Device according to claim 1, wherein the magnet arrangement (30) consists of a magnet (32) and two pole shoes (33, 34) forming an annular gap (36) and having a different magnetic charge, between which end faces (37, 38) a magnetic liquid (31) is arranged, wherein the magnet (32), the pole shoe (33) and/or the pole shoe (34) are fixed on the impeller (9) and/or on the electric motor (2).

8. Device according to claim 7, wherein a pole shoe (33 or 34) is formed in two pieces, separated by a secondary gap (35).

9. Device according to claim 7, wherein the end faces (37, 38) limiting the annular gap (36), between which the magnetic liquid (31) is arranged, are formed mirror symmetrically to each other.

10. Device according to claim 7, wherein the end faces (37, 38) delimiting the annular gap (36) are not formed symmetrically to each other.

11. Device according to claim 7, wherein the end faces (37, 38) have recesses and/or projections formed circumferentially.

12. Device according to claim 7, wherein the end faces (37, 38) are formed planar.

13. Device according to claim 7, wherein the end faces (37, 38) are arranged parallel to each other.

14. Device according to claim 7, wherein the end faces (37, 38) are not arranged parallel to each other.

15. Device according to claim 7, wherein the end faces (37, 38) are arranged at a right angle to the annular gap axis.

16. Device according to claim 7, wherein the end faces (37, 38) are arranged acute-angled and/or obtuse-angled to the annular gap axis.

17. Device according to claim 7, wherein the end faces (37, 38) circumferentially are formed concave and/or convex.

18. Device according to claim 7, wherein the magnets (32) of the magnet arrangement (30) are formed as permanent or electromagnets.

* * * * *